United States Patent
Tracy et al.

(10) Patent No.: US 6,526,980 B1
(45) Date of Patent: Mar. 4, 2003

(54) CERVICAL DRUG DELIVERY SYSTEM

(75) Inventors: Timothy S. Tracy, Morgantown, WV (US); Douglas D. Glover, Morgantown, WV (US); Patrick S. Callery, Morgantown, WV (US); Leo R. Brancazio, Morgantown, WV (US); Barbara L. McFarlin, Morgantown, WV (US); Andrew P. Soisson, Morgantown, WV (US); James E. Smith, Bruceton Mills, WV (US)

(73) Assignee: West Virginia University, Morgantown, WV (US)

( * ) Notice: Subject to any disclaimer, the term of this patent is extended or adjusted under 35 U.S.C. 154(b) by 51 days.

(21) Appl. No.: 09/649,170

(22) Filed: Aug. 25, 2000

Related U.S. Application Data

(60) Provisional application No. 60/150,785, filed on Aug. 26, 1999.

(51) Int. Cl.[7] .................................................. A61F 6/06

(52) U.S. Cl. ........................ 128/830; 128/832; 128/837

(58) Field of Search ................................ 128/830–840; 604/55, 54, 275–279

(56) References Cited

U.S. PATENT DOCUMENTS

| | | | | | |
|---|---|---|---|---|---|
| 4,832,052 A | * | 5/1989 | Mohajer | ...................... | 128/834 |
| 4,993,432 A | * | 2/1991 | Shields | ......................... | 128/838 |
| 5,044,376 A | * | 9/1991 | Shields | ......................... | 128/841 |
| 5,364,375 A | * | 11/1994 | Swor | ........................... | 128/841 |
| 6,139,538 A | * | 10/2000 | Houghton | .................... | 604/515 |
| 6,239,182 B1 | * | 5/2001 | Zaneveld | ..................... | 514/764 |

\* cited by examiner

*Primary Examiner*—Michael A. Brown
(74) *Attorney, Agent, or Firm*—Steptoe & Johnson PLLC

(57) ABSTRACT

An cervical drug delivery apparatus having an absorbent cylindrical structure with a cervical cap attached to one end. One or more therapeutic agents are applied to the internal surface of the cervical cap. The cervical drug delivery apparatus is housed within an applicator and inserted into a patient's vagina. Upon deployment of the cervical drug delivery apparatus, the cervical cap is automatically positioned over the patient's cervix providing for the direct application of the therapeutic agents on the patient's cervix. Alternative features of the cervical drug delivery apparatus include, a break-away cylindrical structure, a collapsible support structure for the cervical cap, an inflatable means for supporting the cervical cap, and the ability of the cylindrical structure and/or the cervical cap to contain one or more therapeutic agents that can be delivered by outside means.

45 Claims, 8 Drawing Sheets

CERVICAL DRUG DELIVERY SYSTEM

RELATED APPLICATIONS

This application claims the benefit of U.S. Prov. patent application Ser. No. 60/150,785, filed Aug. 26, 1999.

FIELD OF THE INVENTION

This invention relates to cervical devices, and more specifically, to a cervical drug delivery apparatus having a concave cap attached to the end of a cylindrical structure for applying and delivering therapeutic agents to a patient's cervix.

RELATED ART

Currently, therapeutic agents, e.g. misoprostol, are delivered to a human cervix by either inserting a tablet or gel directly into the vagina, which exposes both the vagina and cervix to the agent, or by direct injection of the agent into the cervix with a needle. The disadvantage with this procedure, however, is that several agents designed for drug therapy to the cervix are either systemically toxic or cause irritation to the vagina or outer vulva. Other agents given for cervical maladies are creams also inserted into the vagina. The disadvantage with creams is that they often leak out onto the vulva and become extremely irritating and painful.

Therefore, a cervical agent delivery apparatus is needed that provides for the direct administration and delivery of therapeutic agents to the cervix, e.g., anesthetics, anti-virals, anti-neoplastics and cervical ripening agents, while minimizing vaginal and systemic exposure to the agent. Since the cervix is not as highly vascularized as the vagina, direct administration to the cervix would reduce systemic exposure since less drug will be distributed to the body and the desired organ will be specifically targeted.

One example of conventional methods of drug delivery to a patient's cervix involves the administration of anesthetic agents to reduce pain and discomfort prior to cervical dilation or biopsy. Currently, there are no other established methods for administering anesthetic agents to a patient's cervix other than direct injection of the anesthetic via a needle and syringe. Most patient's report this injection to be more painful and uncomfortable than the procedure (which itself is uncomfortable and sometimes painful). Thus, the majority of women, and their physicians, choose to forego any anesthetic agent and thus endure the associated pain.

As another example of conventional methods for cervical drug delivery, Misoprostol, a tablet traditionally used to prevent non-steroidal anti-inflammatory drug induced ulcers in a patient's stomach, is another example of a drug sometimes delivered to the cervix. However, Misoprostol is contra-indicated on its label for use with a pregnant patient because of its effect for inducing labor. In reality, however, physicians often apply misoprostol for its off-label use in the promotion of cervical ripening in pregnancy wherein the physician directly applies a misoprostol tablet to a patient's cervix in order to induce cervical ripeness, thereby inducing labor. There are many disadvantages with using misoprostol for this off-label use. First, this topical use is directly counter to the drug's allowed use. Second, the tablet form of misoprostol is intended for oral ingestion only—not as a topical agent. Therefore, the tablet form occasionally does not dissolve in a vagina. In addition the tablet may be difficult to position properly so as to directly contact the cervix. Lastly and most importantly, the proper dosage of misoprostol has not been ascertained or even studied because this use of misoprostol is a non-labeled use. Therefore, physicians typically use a "hit or miss" dosage until the desired effect is achieved.

Therefore, there is a need for an alternative form of misoprostol, other than tablet form, that can be easily and removably placed in a patient's vagina in direct contact with the cervix. Furthermore, there is a need for this alternative form of misoprostol that can be used with a cervical agent delivery apparatus providing the direct application of misoprostol on a patient's cervix.

Another type of device used in connection with covering a patient's cervix is the cervical cap. For example, the Prentif Cervical Cap® covers a patient's cervix and is used as a barrier method of contraception. Similarly, the Today R contraceptive sponge was a sponge-like device shaped to fit over a patient's cervix thereby also serving as a physical contraceptive barrier. However, the Today R sponge also contained nonoxynol-9 (a spermicidal agent) which was released into the vagina to assist in preventing contraception. A second type of cervical cap is the Instead® (cervical) Cap which is a flexible ring connected to a flexible plastic sac-like reservoir. The ring fits around a patient's cervix wherein the reservoir collects the patient's menstrual flow. This device is not designed to fit closely around the cervix.

Other types of devices used in connection with a patient's cervix consist of a catheter that is inserted through the cervix and into the uterus to allow administration of agents to enhance the contrast seen in the uterus during an ultrasound procedure. An example of this type of device is the Zinnanti Uterine Injector R which is a catheter having a cervical stop to prevent inserting it too far into the patient's uterus. This device is available in 2 and 4 mm sizes, and in dual lumen designs allowing delivery of an agent through one lumen and delivery of air to a balloon-like structure through the second lumen to prevent it from coming out of the uterus.

Therefore, there is a need for a cervical agent delivery apparatus and system for applying and delivering a cervical agent directly to a patient's cervix. There is a further need for a cervical agent delivery apparatus that allows for the treatment of a patient's cervix with a therapeutic agent for an undetermined length of time. There is still a further need for a cervical agent delivery apparatus having a means for supporting the apparatus in the proper position over a patient's cervix.

SUMMARY OF THE INVENTION

The apparatus and system of the present invention solves the problems with conventional means for applying and delivering therapeutic cervical agents to a patient's cervix by providing a flexible or semi-rigid cervical cap made of plastic, rubber or similar material that is attached to a front end of a cylindrical structure of absorbent material, e.g., a tampon, thereby creating a cervical agent delivery apparatus. In operation, a desired therapeutic agent is applied to the internal surface of the cervical cap either prior to shipping, such as by the manufacturer, by hand or by a medicated pad attached to the internal surface of the cervical cap immediately prior to use. Once prepared, medical personnel, or a patient, inserts the apparatus into the patient's vagina, as in a conventional method for using tampons, wherein the front end with the cervical cap is inserted first. Upon insertion of the apparatus, the cervical cap comes in direct contact with the patient's cervix due to the natural positioning of the cylindrical structure. Therefore, the therapeutic agent on the internal surface of the cervical cap is dispersed directly to the cervix for treatment. The apparatus is held in place by conventional means, that is, by the anatomy of the vagina surrounding the cylindrical structure. The cylindrical structure protects the spreading of the therapeutic agent to the vagina and vulva due to its inherent absorbency. The cylindrical structure absorbs that portion of the therapeutic agent that leaks out of the cervical cap and/or off of the cervix. The apparatus of the present invention can either be self-administered by a patient for home use, thereby minimizing health care costs, or can be inserted by a physician.

In one alternative embodiment, the cervical agent delivery apparatus of the present invention further comprises a tube applicator as a means for deploying the apparatus, similar to a conventional tampon applicator. In this embodiment, the entire apparatus (the cylindrical structure and the cervical cap with the cervical agent previously applied) are housed within the applicator wherein the cervical cap is compressed such that it fits within an internal chamber of the applicator. This alternative apparatus is deployed using conventional methods for deploying a tampon. Therefore, upon deployment, the cervical cap opens to its intended form and contacts the patient's cervix with the cervical agent in the intended manner.

In another alternative embodiment, a collapsible support structure surrounds the exterior of the cervical cap to further define and hold the cervical cap's shape. The support structure is collapsible in order to fit within an applicator. In the preferred embodiment, the support structure comprises a plurality of flexible fingers that define the concave shape of a cervix and a cervical cap. In alternative embodiments, the support structure is a flexible rim on the edge of the cervical cap.

In another embodiment, the cylindrical structure, the cervical cap, the support structure surrounding the cervical cap, or any combination thereof may incorporate one or more other therapeutic agents. Therefore, when deployed within a patient, these additional therapeutic agents may leech out in a well known manner and provide further treatment to the patient. For example, the cylindrical structure may contain a neutralizing agent that neutralizes the effects of a therapeutic agent on the internal surface of the cervical cap and protects the areas around the cervix, e.g., the vulva, that are not to receive treatment with the therapeutic agent. This is an important feature especially when the therapeutic agent is an anti-viral agent.

There are many advantages associated with the cervical agent delivery apparatus and system of the present invention. The apparatus ensures the direct application and delivery of a therapeutic agent to a patient's cervix. By having an absorbent cylindrical structure which absorbs any excess therapeutic agent, the patient's vagina and vulva are protected from undesired exposure to the therapeutic agent. The low-tech nature of the apparatus and its conventional deployment ensures that practically anyone can deploy the apparatus with success. As a result, health care costs are minimized because the apparatus may be used by patients at home. Lastly, a patient can receive multiple types of treatment with a single use of the apparatus when the apparatus incorporates two or more therapeutic agents.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENTS

Figure 1:
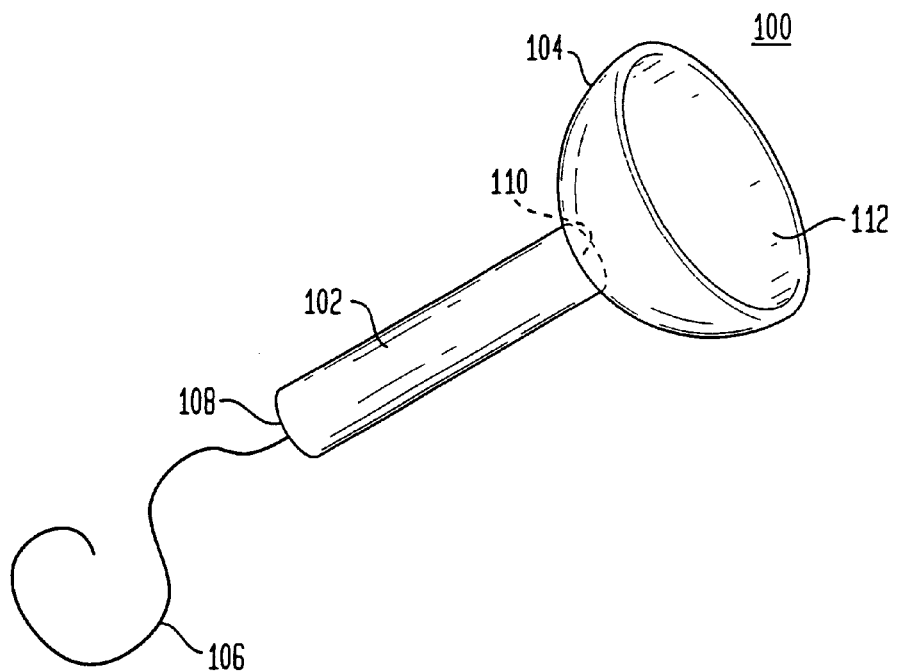
FIG. 1 is a perspective view of a cervical agent delivery apparatus of the present invention.

A cervical agent delivery apparatus, or "apparatus," 100 of the present invention is shown in FIG. 1. In the preferred embodiment, the apparatus 100 is a cylindrical structure 102 having a front end 110 and a back end 108 with a string 106 used for removal of the apparatus 100 securely attached to the back end 108. A cervical cap 104 is permanently attached to the front end 110 of the cylindrical structure 102, e.g., with adhesive, or molded as a single component. The preferred embodiment of the cylindrical structure 102 is an elongated cylinder made of an absorbent material, e.g., cotton. For example, a conventional tampon may be used. The cylindrical structure 102 of the present invention is described in terms of a tampon-like structure for convenience purpose only. It would be readily apparent to one of ordinary skill in the relevant art to use a comparable structure.

Also in the preferred embodiment, the cervical cap 104 of the present invention is similar in design to a conventional diaphragm and provides the means for dispensing a cervical agent, e.g., a therapeutic drug, to a patient's cervix. The cervical cap 104 is described and shown in terms of a diaphragm for convenience purpose only. In the preferred embodiment, the cervical cap 104 is a thin flexible piece of rubber with or without a rim being concave in shape and being about 30–90 mm in diameter. It would be readily apparent for one of ordinary skill in the relevant art to use a comparable means for dispensing, e.g., a sponge. The means for dispensing must be shaped to contact, and preferably, cover a patient's cervix, or be flexible enough to encompass a patient's cervix. Therefore, upon contact with a cervix, the means for dispensing will ensure that the cervix agent is applied properly and to the proper location.

In operation, one or more therapeutic agents are delivered to and deposited on the internal surface 112 of the cervical cap 104. A manufacturer may apply the therapeutic agent(s) to the cervical cap 100 prior to shipping, or medical personnel or the patient may apply the therapeutic agent(s) immediately prior to its use. Once prepared, the apparatus 100 is inserted into a patient's vagina as is a conventional tampon. Due to the natural positioning of the cylindrical structure 102 within a patient, the cervical cap 104 directly contacts the patient's cervix. When the application of the therapeutic agent is complete, the apparatus 100 is removed by conventional means of removing a tampon, that is, by pulling on the string 106 at the back end 108 of the cylindrical structure 102. The apparatus 100 is then disposed of.

Figure 2:
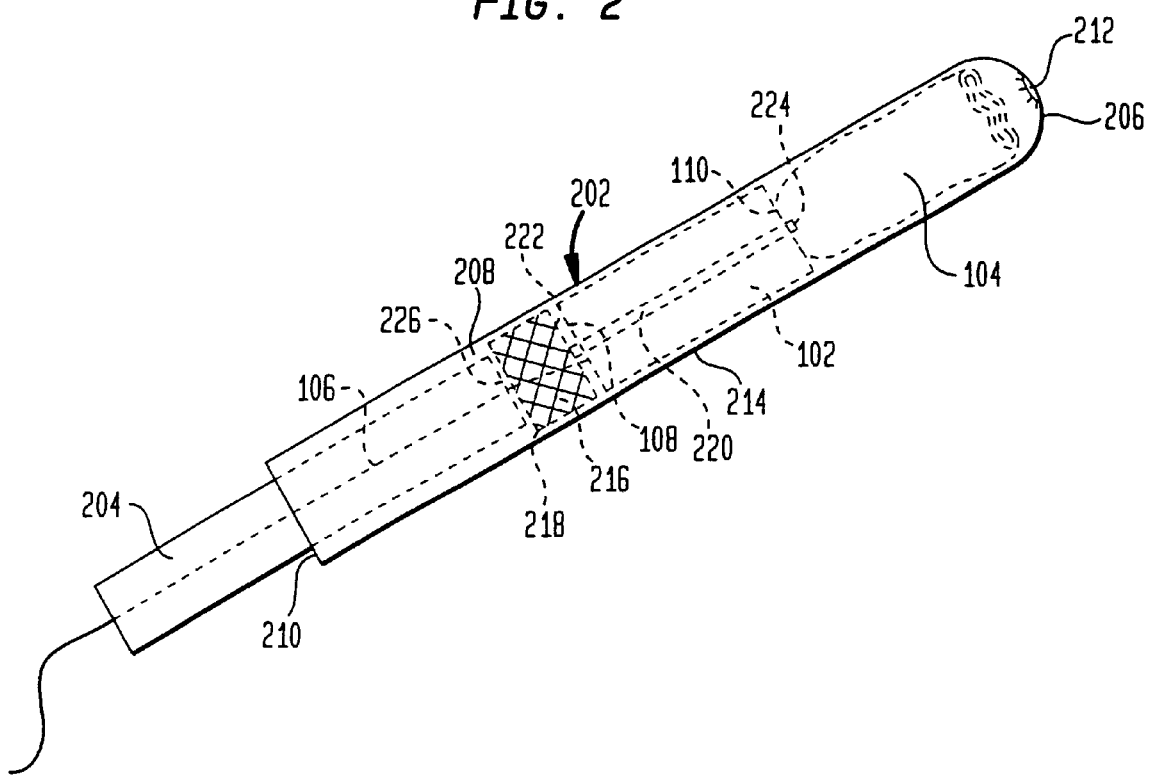
FIG. 2 is a perspective view of the cervical agent delivery apparatus within an applicator.
Figure 3:
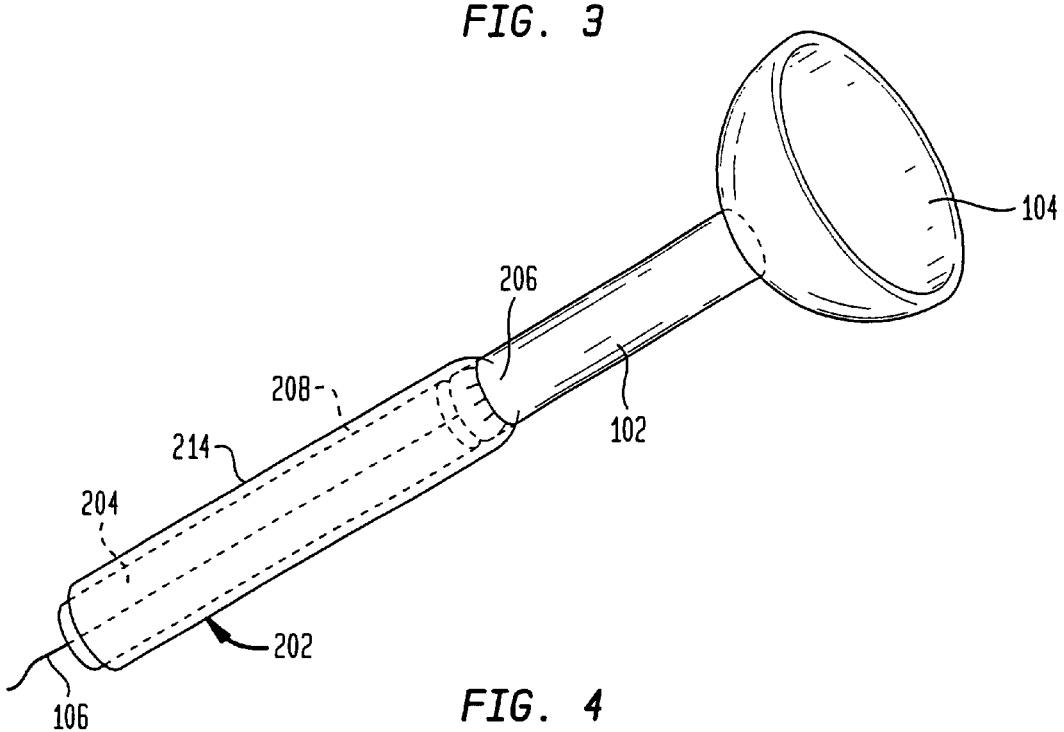
FIG. 3 is a perspective view of the cervical agent delivery apparatus deployed from the applicator.
Figure 4:
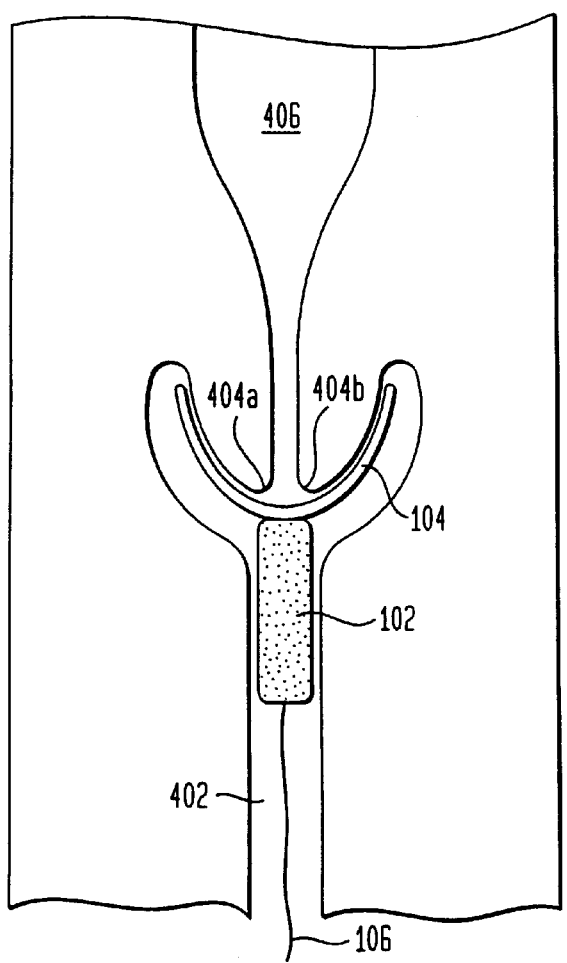
FIG. 4 is a planar cross sectional view of the cervical agent delivery apparatus in use.

The preferred means for inserting and deploying the cervical agent delivery apparatus 100 is an applicator 202 as shown in FIG. 2. FIG. 3 is a perspective view of the cervical agent delivery apparatus 100 as deployed from the applicator 202, and FIG. 4 shows the cervical agent delivery apparatus 100 in use within a patient.

The preferred embodiment of the applicator 202 is similar in design and operation to a conventional tampon applicator. The applicator 202 is an elongated hollow tube 208 having an internal chamber 208, an open end 210, and an application end 206 which is primarily closed except for a means for opening 212, e.g., a perforated opening as shown, centrally located on the application end 206. The applicator 202 also comprises an elongated rod 204 that fits within the elongated hollow tube 202 and passes through the open end 210. The elongated rod 204 is a means for deploying the apparatus 100 of the present invention stored within the internal chamber 208 of the applicator 202.

The applicator 202 may also have a reservoir chamber 218 in the internal chamber 208 that contains one or more therapeutic agents 216 and is positioned between the front end 226 of the elongated rod 204 and the back end 108 of the cylindrical structure 102. The reservoir chamber 218 is made of a flexible material that compresses upon the application of pressure by the elongated rod 204. An elongated tube 220 having a front end 224 and a back end 222 connects the reservoir chamber 216 with the internal surface 112 of the cervical cap 104, wherein the front end 224 of the elongated tube 220 is connected to the cervical cap 104 and the back end 222 of the elongated tube 220 is connected to the reservoir chamber 218.

In this embodiment using a reservoir chamber 218, the therapeutic agent(s) 216 are delivered to the internal surface 112 of the cervical cap 104 when the elongated rod 204 is pushed inwards to deploy the apparatus 100. Specifically, the front end 226 of the elongated rod 204 presses against and compresses the reservoir chamber 218, thereby pushing the therapeutic agent(s) 216 through the elongated tube 220 and into the internal surface 112 of the cervical cap 104. After the reservoir chamber 220 has been emptied, the front end 226 of the elongated rod 204 and the emptied reservoir chamber 218 push against the back end 208 of the cylindrical structure 102 until the apparatus 100 is deployed from the applicator 202.

In an embodiment without the reservoir chamber 218 and elongated tube 220, a therapeutic agent is delivered and applied to the internal surface 112 of a cervical cap 104 of an apparatus 100 as described above, either by the manufacturer prior to shipping or by hand immediately before use wherein a person ejects the therapeutic agent into the cervical cap 104. The apparatus 100 is then housed within the internal chamber 208 of the applicator 202 by conventional means. Then, to deploy the apparatus 100, a physician, other medical personnel, or the patient, inserts the applicator 202 according to known methods into the patient's vaginal cavity 402 and pushes the elongated rod 204 which in turn pushes the apparatus 100 through the perforated opening 212 of the application end 206 of the applicator 202. Once deployed, the cervical cap 104 returns to its natural concave shape and contacts the cervix 404a,b, thereby covering the cervix 404a,b and applying the cervical agent. The applicator 202 is then removed from the patient and discarded while the cervical agent delivery apparatus 100 remains within the patient. The applicator 202 is described in terms of a conventional tampon-like applicator for convenience purpose only. It would be readily apparent to one of ordinary skill in the relevant art(s) to use another conventional means for inserting an apparatus 100, e.g., manual deployment or with a comparable insertion device.

Alternatively, the applicator 202 is not removed from the patient, but rather remains in the patient during treatment. After the treatment of the therapeutic agent is complete, the cervical agent delivery apparatus 100 is retracted back into the applicator 202. The applicator 202 with the cervical agent delivery apparatus 100 is removed and discarded. The advantage to retracting the cervical agent delivery apparatus 100 back into the applicator 202 is that it reduces the exposure of the vagina and vulva to the therapeutic agent.

The applicator 202 of the present invention is intended to be disposable, and accordingly is made of any appropriate material, including plastic, heavy paper, etc. In one embodiment, the applicator 202 is made of a clear plastic to allow a physician or medical personnel the ability to direct the placement of the cervical agent delivery apparatus 100 and/or observe the effects of the cervical agent delivery apparatus 100 within a patient.

According to the specific treatment, the cervical drug delivery apparatus 100 may be kept within the patient for the needed length of time to fully treat the patient's cervix 404a,b. In the preferred embodiment, the apparatus 100 may be kept in for any time duration ranging from minutes to hours, with a preferred maximum duration of 24 hours. The duration of insertion of the apparatus 100 is described in these terms for convenience purpose only. It would be readily apparent for one of ordinary skill in the relevant art to determine the appropriate time for removing the apparatus by closely monitoring the patient's condition.

Figure 5:
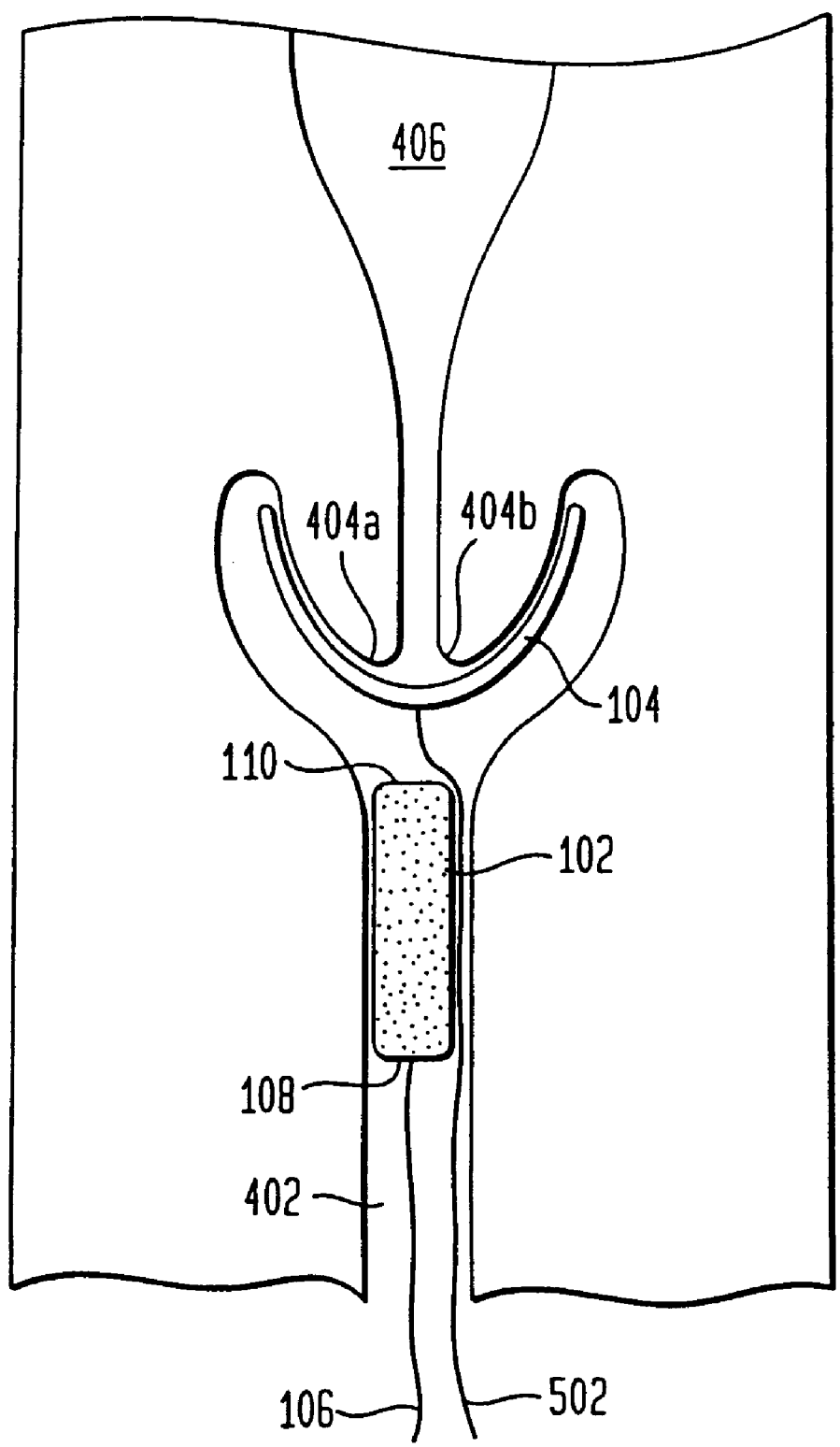
FIG. 5 is a planar cross sectional view of an alternative cervical agent delivery apparatus.

An alternative cervical agent delivery apparatus 100 is shown in FIG. 5 wherein the cervical cap 104 is detachable from the cylindrical structure 102. In this embodiment, the cervical cap 104 is secured to the front end 110 of the cylindrical structure 102 by a light adhesive, or snap or comparable means for attaching, that is strong enough to hold the cervical cap 104 during deployment of the apparatus 100 and application of the cervical cap 104 to the patient's cervix 404a,b, yet light enough that with a quick twist or pull of the cylindrical structure 102, the cylindrical structure 102 breaks free from the cervical cap 104 and leaves the cervical cap 104 in place over the patient's cervix 404a,b.

Once the cylindrical structure 102 has broken free from the cervical cap 104, the cylindrical structure 102 is removed from the patient by pulling on the string 106. Therefore, the cervical cap 104 remains in position covering the patient's cervix 404a,b as long as needed for proper treatment of the therapeutic agent. When the treatment is complete, the cervical cap 104 is removed from the patient by pulling on a cervical cap string 502 that is securely attached to the exterior of the cervical cap 104.

This alternative embodiment of the apparatus 100 also can be used with an applicator 202 described above. The cylindrical structure 102 with the cervical cap 104 attached thereto are housed in the internal chamber 208 of an applicator 202 with the cervical cap string 502 extending along the exterior of the cylindrical structure 102 and through the open end 210 of the applicator 202 with the string 106.

Figure 6:
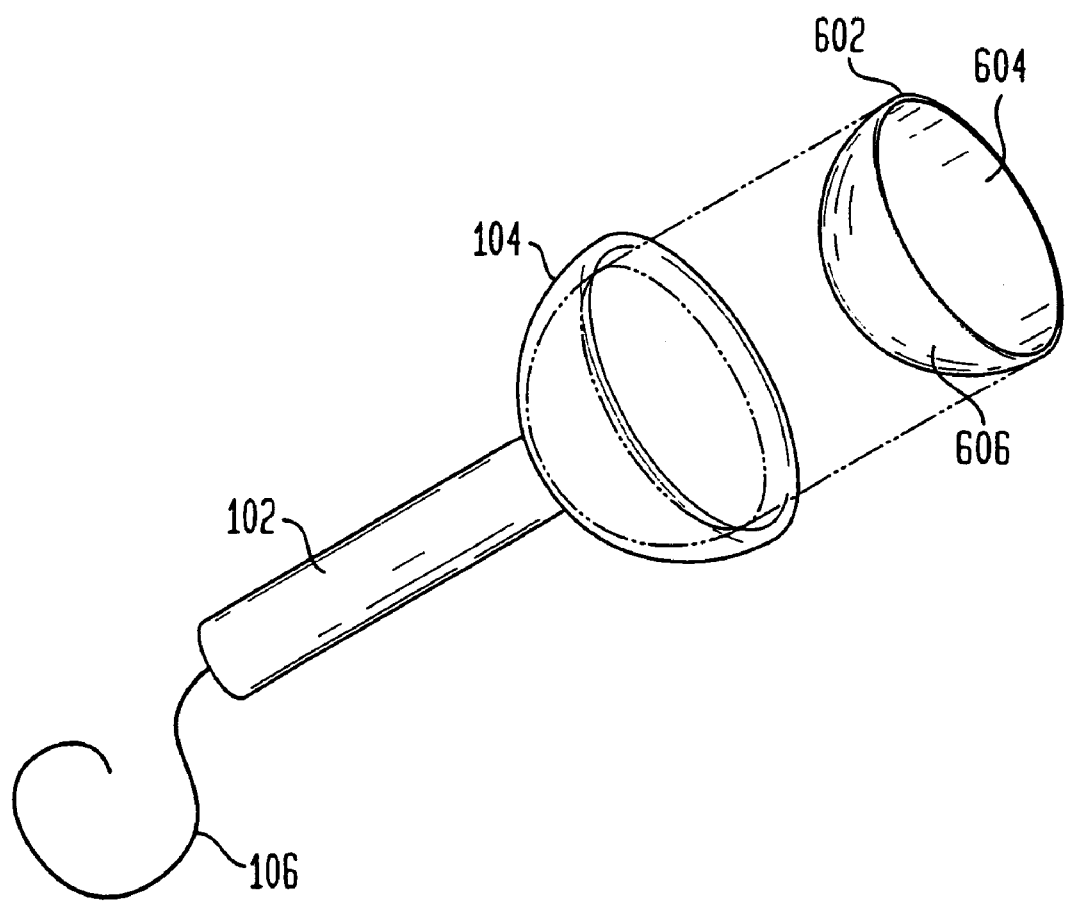
FIG. 6 is a perspective view of the cervical agent delivery apparatus with an attachable medicated pad.

The cervical agent delivery apparatus 100 of the present invention also can be used with an attachable medicated pad 602 as shown in FIG. 6. In the preferred embodiment, the medicated pad 602 is an absorbent gauze pad containing a therapeutic agent. The use of a gauze pad is for convenience purpose only. It would be readily apparent to one of ordinary skill in the relevant art(s) to use any material that is needed for a specific therapeutic agent or treatment procedure. The preferred medicated pad 602 has an adhesive on its exterior surface 606 that enables the medicated pad 602 to be secured to the interior surface 112 of the cervical cap 104. The therapeutic agent of the medicated pad 602 may be either different from or the same as the therapeutic agent on the cervical cap 104. In addition, it may be a therapeutic agent that complements or enhances the effectiveness of the therapeutic agent on the cervical cap 104. In operation, a therapeutic agent is put on a medicated pad 602, if not already done, and the medicated pad is adhered to the internal surface 112 of the cervical cap 104. The cervical agent delivery apparatus 100 is then used as described above.

Figure 7:
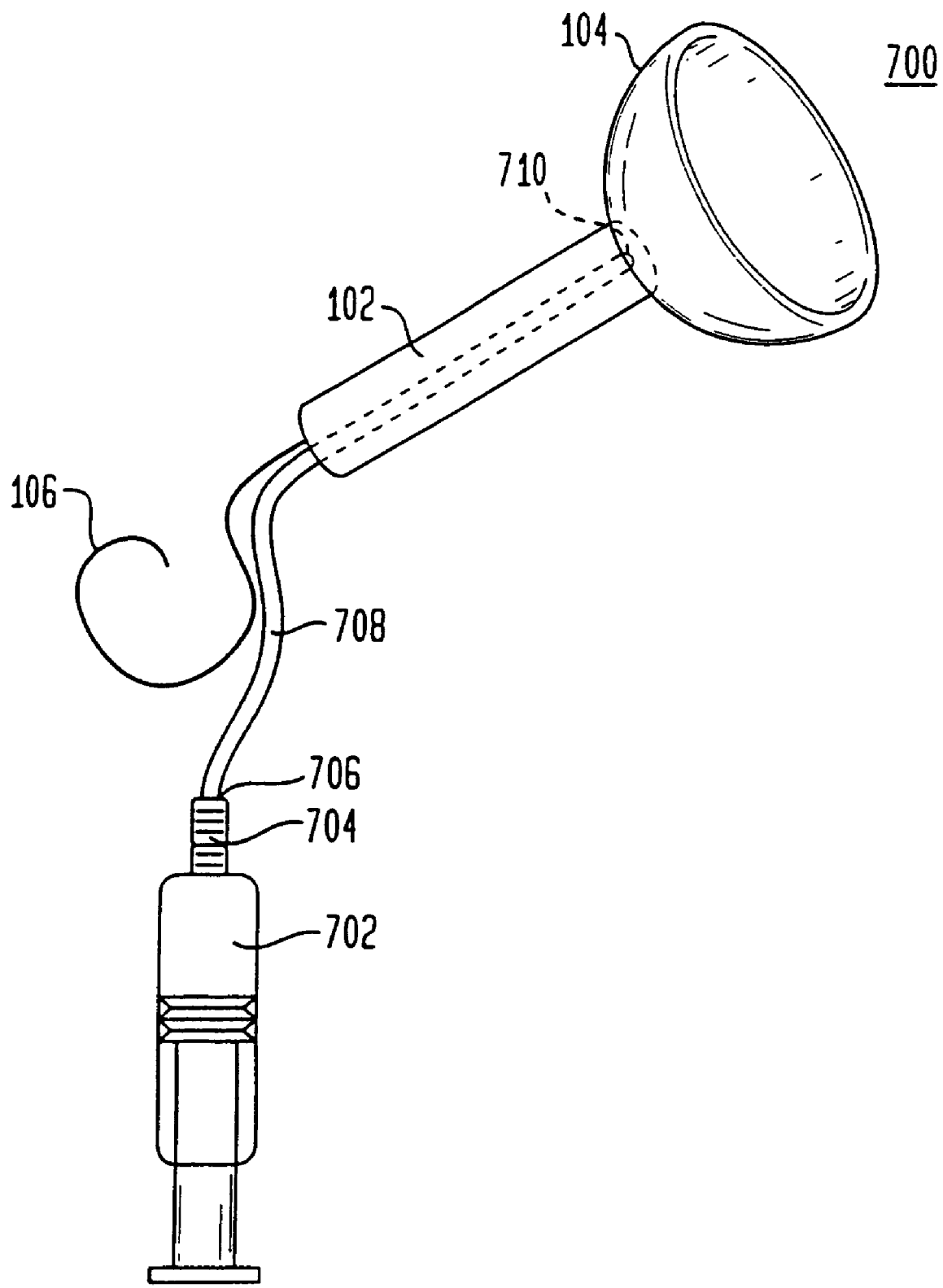
FIG. 7 is a perspective view of an alternative cervical agent delivery apparatus.

FIG. 7 is a perspective view of a cervical agent delivery apparatus 700 having an alternative means for delivering a therapeutic agent onto the internal surface of the cervical cap 104. In this embodiment, an elongated tube 708 having a first end 706 and a second end 710 connects a syringe 702 to the interior surface 112 of the cervical cap 104. The syringe 702 is removably attached to the first end 706 of the elongated tube 708 via a conventional coupler 704. The second end 710 of the elongated tube 708 passes longitudinally through the cylindrical structure 102 and through the cervical cap 104 until it opens on the internal surface 112 of the cervical cap 104.

In operation, the syringe 702 and elongated tube 708 are used as a means for delivering one or more therapeutic agents into the cervical cap 104. After the cervical agent delivery apparatus 700 is properly positioned within a patient, a syringe 702 containing the therapeutic agents is coupled to the first end 706 of the elongated tube 708. The therapeutic agents are then delivered through the elongated tube 708 via the syringe 702 and onto the internal surface 112 of the cervical cap 104. The use of a syringe 702 is for convenience purpose only. It would be readily apparent to one of ordinary skill in the relevant art to use a comparable means for delivering therapeutic agents, such as a pump or bulb-type device.

Alternatively, the syringe 702 and elongated tube 708 described above can be used as a means for collecting specimens from several areas within the patient, including but not limited to the ecto-cervix, endo-cervix, and the uterus. In this use, the physician or medical personnel draws back on the syringe 702 to draw specimens through the elongated tube 708 from the cervical cap 104. The specimens are then tested and analyzed to provide a complete diagnosis of and proper treatment to the patient.

Figure 8:
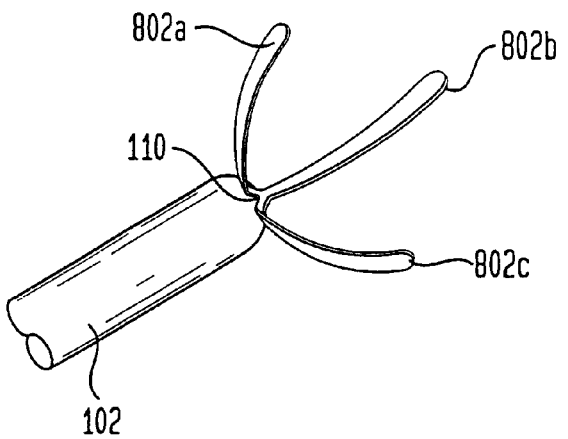
FIG. 8 is a perspective view of a collapsible support structure attached to the front end of a cylindrical structure of the present invention.

A cervical agent delivery apparatus 100 also may incorporate a collapsible support structure 802 attached to the front end 110 of a cylindrical structure 102 of the present invention as shown in FIG. 8. In this embodiment, the collapsible support structure 802 comprises three or more fingers 802*a–c* made of flexible, memory plastic. The fingers 802 are bendable such that when housed in an applicator 202, the fingers 802*a–c* bend, or collapse, forward. Then, upon deployment, the fingers 802*a–c* return to their original, intended shape, providing the framework for supporting the cervical cap 104 of the apparatus 100. In the preferred embodiment, the fingers 802*a–c* are made of plastic and are permanently attached to the front end 110 of the cylindrical structure 102 via glue or similar adhesive or means for securely attaching the collapsible support structure 802. The use of plastic and an adhesive is for convenience purpose only. It would be readily apparent to one of ordinary skill in the relevant art(s) to use a comparable material, e.g., a composite material, fibrous material, or flexible rubber, or means for attaching the fingers 802*a–c*, e.g., a clip, pin, tie, or other type of fastener.

Figure 9:
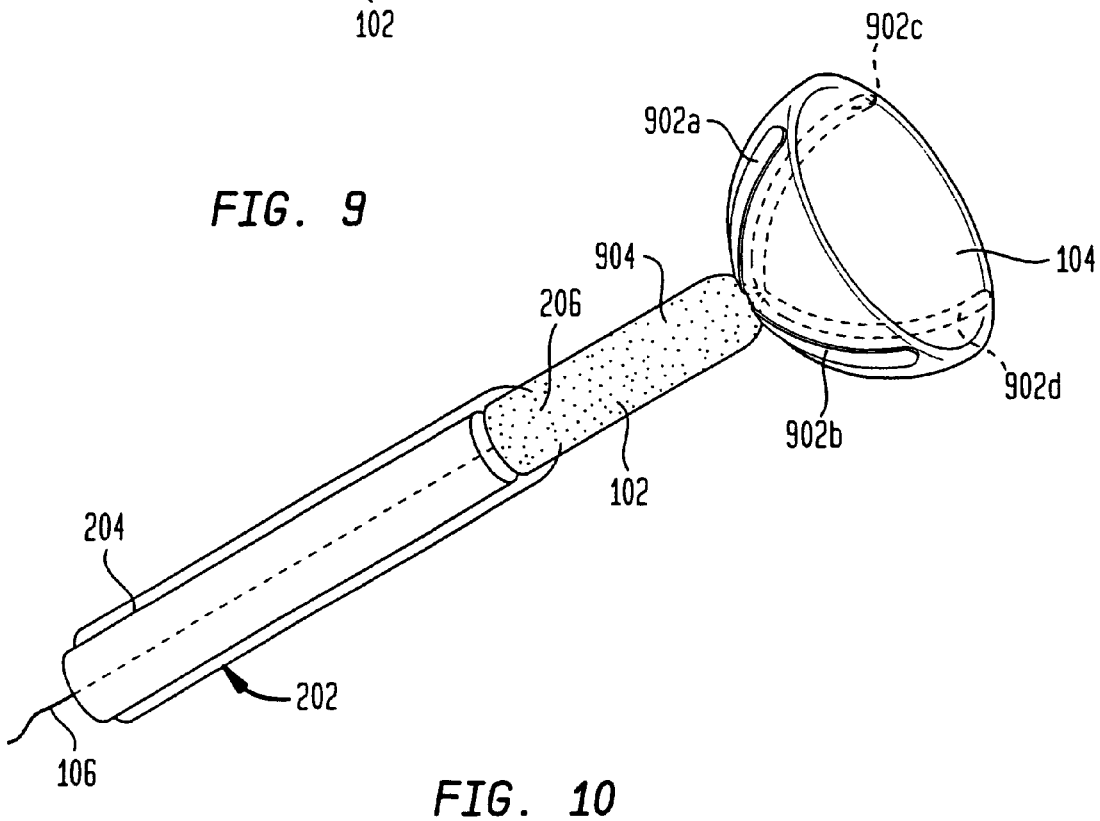
FIG. 9 is a perspective view of an alternative cervical agent delivery apparatus having the collapsible support structure encompassing the cervical cap.

FIG. 9 shows a collapsible support structure 902 having four fingers 902*a–d* encompassing a cervical cap 104 that, upon deployment, return to their concave shape and support the cervical cap 104. As discussed above, in the preferred embodiment the fingers 902*a–d* are made of plastic.

Figure 10:
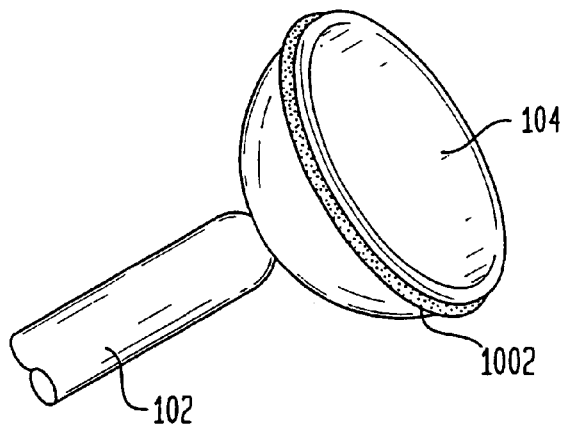
FIG. 10 is a perspective view of an alternative collapsible support structure.

An alternative collapsible support structure 1002 is shown in FIG. 10. In this embodiment, the collapsible support structure 1002 is a flexible rim 1002 on the outer edge of the cervical cap 104. The flexible rim 1002 collapses when the apparatus is housed within an applicator 202 and then, upon deployment, returns to its original shape and supports the cervical cap 104. Other alternate forms of a collapsible support structure may include a combination of fingers 802, 902 and rim 1002.

Figure 11:
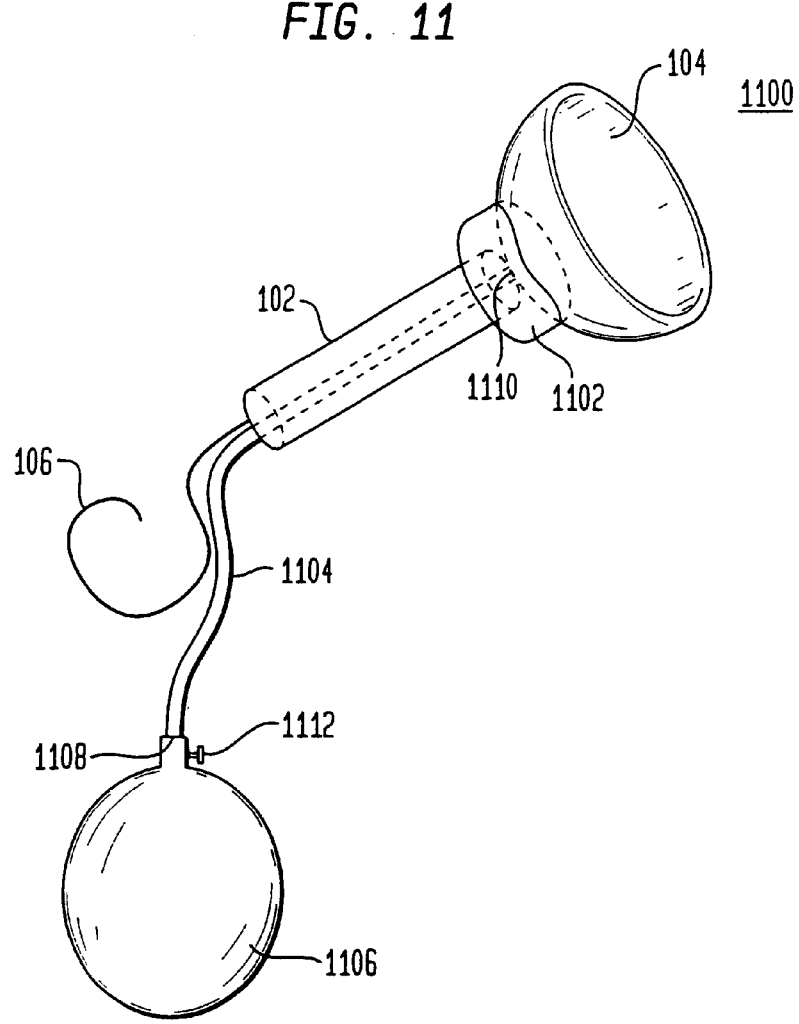
FIG. 11 is a perspective view of an alternative cervical agent delivery apparatus having an inflatable means positioned behind the cervical cap.
Figure 12:
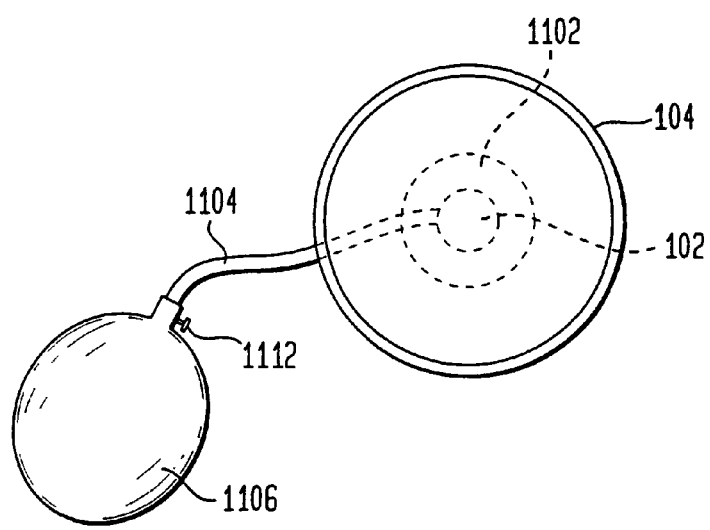
FIG. 12 is a top planar view of the alternative cervical agent delivery apparatus having an inflatable means.
Figure 13:
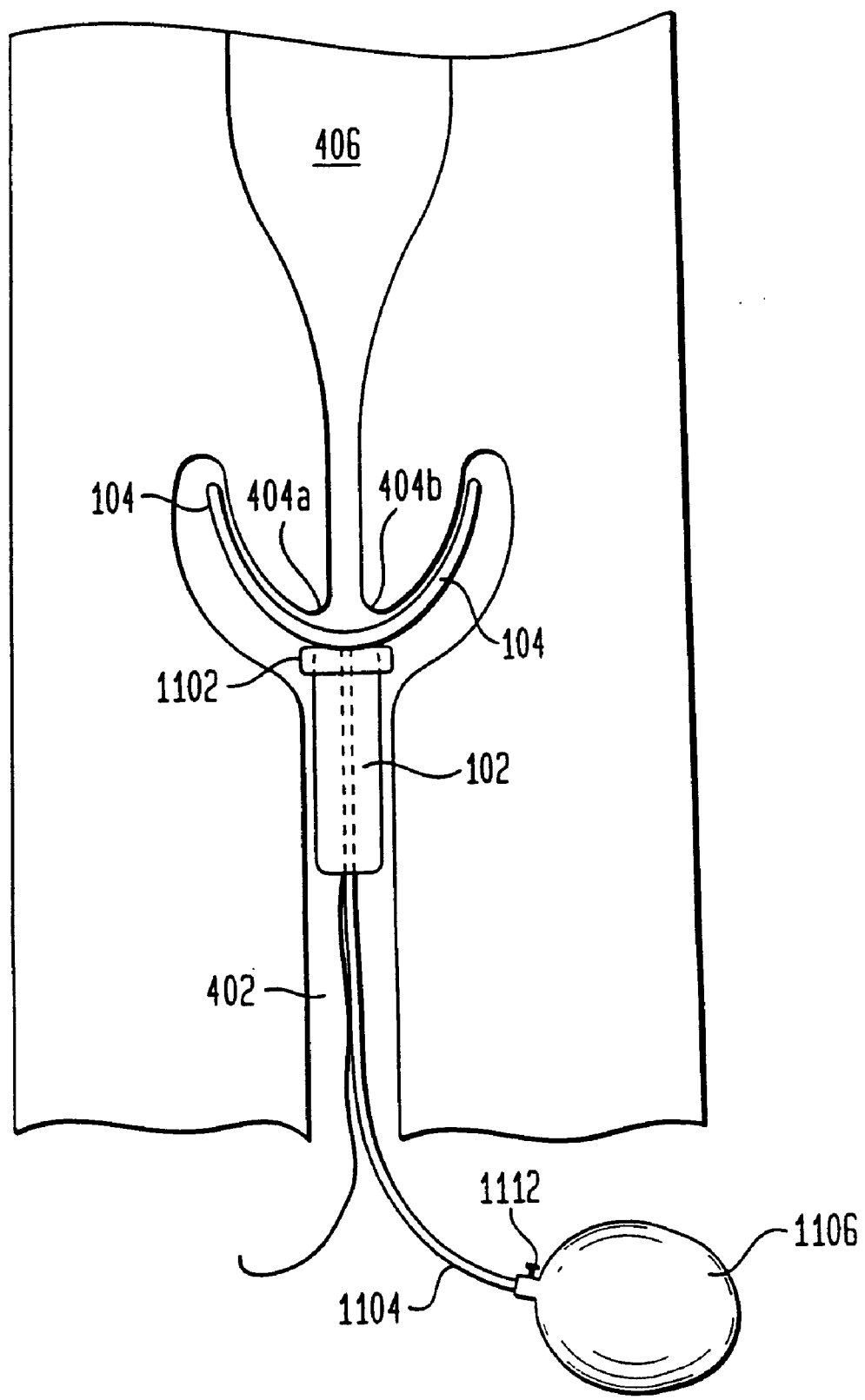
FIG. 13 is a planar cross sectional view of the alternative cervical agent delivery apparatus having an inflatable means in use.

In another alternative embodiment as shown in FIGS. 11–13, a cervical agent delivery apparatus 1100 has an inflatable means positioned behind the cervical cap 104. In this embodiment, an inflatable ring 1102 is attached to the front end 110 of the cylindrical structure 102 directly behind the cervical cap 104. An elongated tube 1104 having a first end 1108 connected to a bulb 1106 and a second end 1110 connected to the inflatable ring 1102 is used to inflate the inflatable ring 1102.

In operation, after the cervical agent delivery apparatus 1100 is deployed as described above, the physician or medical personnel squeezes the bulb 1106 to inflate the inflatable ring 1102 and uses a valve 1112 to maintain the inflation. The inflatable ring 1102 supports the cervical cap 104 and holds it in place and in proper position over the patient's cervix 404*a,b*. After the treatment is complete, the air is let out of the inflatable ring 1102 by opening the valve 1112. Then, the apparatus 1100 is removed by pulling the string 106.

In alternative embodiments of the present invention, one or more components of the apparatus 100 may incorporate one or more different therapeutic agents for treating a patient's vagina, cervix, or related anatomy. For example, the cervical cap 104 and/or the cylindrical structure 102 may be fully impregnated with one or more therapeutic agents 904, as shown in FIG. 9. Alternatively, the cylindrical structure 102 may be divided into two or more regions wherein each region may or may not be impregnated with a different therapeutic agent. In yet another embodiment, the cylindrical structure 102 may contain a neutralizing agent that neutralizes a therapeutic agent on the cervical cap 104. Then any excess therapeutic agent that leaks from the cervical cap 104 is immediately neutralized by the agent in the cylindrical structure 102, thereby protecting the area, e.g., the vulva, surrounding the patient's cervix.

In addition, any embodiment of the collapsible support structure 802, 902, 1002 may also be impregnated with one or more therapeutic agents. For example, one or more of the fingers 902a–d may be impregnated with a therapeutic agent such that upon deployment, the therapeutic agent(s) leech out of the plastic fingers 902a–d in a well known manner and treat the contacting tissue.

It is intended that the apparatus 100 of the present invention be used with therapeutic agents such as Misoprostol, lidocaine, Aldara®, or any anesthetic or anti-neoplastic. In the preferred embodiment, the apparatus 100 of the present invention is used with a cervical ripening compound wherein the cervical ripening compound is deposited on the internal surface of the cervical cap 104 of the apparatus 100. Then, the apparatus 100 is used in its intended manner to apply the cervical ripening compound to a pregnant woman's cervix 404a,b, in order to induce labor. The use of the apparatus 100 with such a compound is advantageous in that the compound is only applied to the cervix 404a,b, thereby preventing unwanted contact with the surrounding area. In addition, when labor is progressing as desired, a physician or other medical personnel can simply remove the apparatus 100 by pulling on the string 106 attached to the cylindrical structure 102, thereby removing the cervical ripening agent from direct contact with the patient's cervix 404a,b. Once removed, the induced labor will immediately begin to slow and maintain a desired state. Therefore, the use of the apparatus 100 of the present invention with a cervical ripening agent provides the means for a physician to directly control a patient's rate of labor while minimizing the use and undesired contact of the agent.

In the preferred embodiment, the cervical ripening agent is a combination of the therapeutic drug misoprostol in a topical application vehicle, or medium. As discussed above, conventional uses of this therapeutic drug only entail the tablet form of misoprostol and are not recommended for use with pregnancies. In the present invention, Misoprostol is present in a topical medium, including, but not limited to, creams, foams, gels, or suspension mediums. Further, the misoprostol is used within the range of about 25–100 micrograms. This form and use of Misoprostol is unique and provides the means for using Misoprostol with pregnant patients.

In operation, this cervical ripening agent, as applied with the cervical drug delivery apparatus 100, maintains contact with a patient's cervix for about 1–2 hours, and no longer than 24 hours. The exact duration of contact is determined by the patient's response to the application of the drug, and it would be readily apparent to one of ordinary skill in the relevant art(s) to determine when to remove the apparatus 100 from the patient.

The cervical agent delivery apparatus 100 of the present invention may be used with many other types of therapeutic agents and for many different types of treatments. The following table illustrates, but is not limited to, possible fields of use of the present invention and potential therapeutic agents:

| Field of Use - Delivery of Agent | Ex's of Fields of Use | Potential Therapeutic Agents |
| --- | --- | --- |
| To the ectocervix | Local anesthesia for biopsies Treatment of cervical dysplasia Cervical ripening Contraception | Lidocaine & other local anesthetics Aldara Misoprostol Spermicides, e.g., nonoxynol-9 |

| Field of Use - Delivery of Agent | Ex's of Fields of Use | Potential Therapeutic Agents |
| --- | --- | --- |
| To the endocervix | Local anesthesia for biopsies | Lidocaine & other local anesthetics |
| To internal organs | Local anesthesia for biopsies | Lidocaine & other local anesthetics |
| To the vagina and ectocervix | Treatment of vaginal fugal infections Treatment of bacterial vaginosis and vaginal trichomonas Local anesthesia for biopsies and vaginal and cervical procedures Treatment of vaginal and cervical dysplasia and cancer Hormonal Therapy | Antifugals, e.g., terconazole Anti-infectives, e.g., metronidazole, sulfa cream, etc. Lidocaine & other local anesthetics Anti-neoplastics/anti-hyperplastic agents, e.g., Aldara ®, 5-fluorouracil, interferons, etc. Estrogens and progestins |
| To the whole body through the the vagina and cervix | Treatment of nausea Hormonal Therapy Nutritional and Vitamin Therapy | Anti-emetics, e.g., ondansetron, prochlorperazine, etc. Estrogens and progestins |
| To the uterus | Treatment of post-partum bleeding Treatment of uterine infection Treatment of uterine bleeding during Depo-Provera ® therapy | Vasopressors Anti-infectives Estrogens |

CONCLUSION

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A cervical agent delivery apparatus, comprising:

a cylindrical structure of absorbent material having a front end and a back end; and a means for dispensing one or more cervical agents to a cervix of a patient, said means for dispensing attached to the front end of said cylindrical structure.

2. The cervical agent delivery apparatus according to claim 1, wherein said means for dispensing the one or more cervical agents is a sponge adapted for receiving the cervical agent.

3. The cervical agent delivery apparatus according to claim 1, wherein said means for dispensing the one or more cervical agents is a cervical cap being generally concave in shape and adapted for receiving the one or more cervical agents on an internal surface.

4. The cervical agent delivery apparatus according to claim 3, wherein said cervical cap is within the range of 30–90 mm in diameter.

5. The cervical agent delivery apparatus according to claim 3, wherein said cervical cap is a flexible composite material.

6. The cervical agent delivery apparatus according to claim 3, wherein said means for dispensing one or more cervical agents further comprises:
   an elongated tube passing through said cervical cap to said internal surface; and
   a means for delivering the one or more cervical agents through said elongated tube to said cervical cap.

7. The cervical agent delivery apparatus according to claim 6, wherein said means for delivering is a syringe.

8. The cervical agent delivery apparatus according to claim 6, wherein said means for delivering is a bulb.

9. The cervical agent delivery apparatus according to claim 6, wherein said elongated tube passes through said cylindrical structure.

10. The cervical agent delivery apparatus according to claim 3, further comprising a medicated pad having an exterior surface adapted to attach to said internal surface of said cervical cap.

11. The cervical agent delivery apparatus according to claim 1, wherein at least one said cervical agent is selected from the group of misoprostol, lidocaine, aldara, antineoplastic, local anesthetic, anti-fungal, anti-infectives, estrogens, progestins, spermicides, and anti-emetics.

12. The cervical agent delivery apparatus according to claim 1, further comprising a means for removing the cervical agent delivery apparatus from a patient.

13. The cervical agent delivery apparatus according to claim 2, wherein said means for removing is a string attached to the back end of said cylindrical structure.

14. The cervical agent delivery apparatus according to claim 1, wherein said means for dispensing the one or more cervical agents to the cervix further comprises a collapsible support structure.

15. The cervical agent delivery apparatus according to claim 14, wherein said collapsible support structure is a plurality of flexible fingers attached to said front end of said cylindrical structure and in contact with means for dispensing such that said collapsible support structure supports said means for dispensing.

16. The cervical agent delivery apparatus according to claim 14, wherein said collapsible support structure is made of flexible, memory plastic.

17. The cervical agent delivery apparatus according to claim 14, wherein said collapsible support structure is embedded within said means for dispensing the one or more cervical agents.

18. The cervical agent delivery apparatus according to claim 14, wherein said collapsible support structure is a flexible rim on an outer edge of said means for dispensing the one or more cervical agents.

19. The cervical agent delivery apparatus according to claim 14, wherein said collapsible support structure is impregnated with one or more cervical agents.

20. The cervical agent delivery apparatus according to claim 1, wherein said cylindrical structure contains one or more cervical agents.

21. The cervical agent delivery apparatus according to claim 1, wherein said means for dispensing is removably detachable from said front end of said cylindrical structure.

22. The cervical agent delivery apparatus according to claim 21, wherein said means for dispensing comprises a means for removing said means for dispensing from the patient.

23. The cervical agent delivery apparatus according to claim 22, wherein said means for removing said means for dispensing is a string.

24. The cervical agent delivery apparatus according to claim 1, further comprising:
   an applicator having an elongated rod and an elongated hollow tube with an internal chamber, an open end, and an application end, wherein said elongated rod fits within said elongated hollow tube and said cylindrical structure with said means for dispensing the one or more cervical agents is housed within said internal chamber of said elongated hollow tube such that said means for dispensing is aligned with the application end of said elongated hollow tube.

25. The cervical agent delivery apparatus according to claim 24, wherein said application end is a perforated opening.

26. The cervical agent delivery apparatus according to claim 24, wherein said applicator is clear plastic.

27. The cervical agent delivery apparatus according to claim 24, further comprising:
   a reservoir chamber adapted for holding one or more therapeutic agents;
   an elongated tube having a front end and a back end, wherein said front end is connected to said means for dispensing and said back end is connected to said reservoir chamber,
   wherein upon application of pressure to said elongated rod, the one or more therapeutic agents are delivered from said reservoir chamber though said elongated tube to said means for dispensing.

28. A cervical agent delivery apparatus, comprising:
   a cylindrical structure having a front end and a back end, wherein said cylindrical structure contains at least one neutralizing agent; and
   a means for dispensing one or more cervical agents to a cervix of a patient, said means for dispensing attached to the front end of said cylindrical structure.

29. A cervical agent delivery apparatus, comprising:
   a cylindrical structure having a front end and a back end;
   a means for dispensing one or more cervical agents to a cervix of a patient, said means for dispensing attached to the front end of said cylindrical structure; and
   an inflatable means for supporting said means for dispensing the one or more cervical agents.

30. The cervical agent delivery apparatus according to claim 29, wherein said inflatable means for supporting is an inflatable ring attached to said front end of said cylindrical structure, an elongated tube having a first end connected to a bulb and a second end connected to said inflatable ring.

31. A cervical ripening compound for use with a pregnant woman to induce labor, comprising:
   about 25 to 100 micrograms of Misoprostol; and
   a topical application vehicle.

32. The cervical ripening compound according to claim 31, wherein said topical application vehicle is selected from the group of gel, cream, foam, or suspension medium.

33. The cervical ripening compound according to claim 31, wherein the cervical ripening compound is applied to an internal surface of a cervical cap, said cervical cap attached to a front end of a cylindrical structure.

34. A method for dispensing one or more cervical agents to a patient's cervix, comprising the steps of:
   a. inserting an applicator having an elongated rod and an elongated hollow tube with an internal chamber housing a cervical agent delivery apparatus into a patient's vaginal canal, said cervical agent delivery apparatus having a cylindrical structure with a front end and a back end, and a cervical cap having an internal surface and being generally concave in shape, wherein said cervical cap is attached to said front end of said cylindrical structure and is adapted for having one or more cervical agents on said internal surface;

b. pushing said elongated rod of said applicator until said cervical agent delivery apparatus is deployed such that said cervical cap covers the patient's cervix; and c. removing said applicator from the patient.

35. The method according to claim 34, further comprising the step of:

d. removing said cervical agent delivery apparatus from the patient.

36. The method according to claim 34, further comprising the step of:

d. attaching a medicated pad to said internal surface of said cervical cap prior to said step (a), wherein said medicated pad contains one or more therapeutic agents.

37. The method according to claim 34, wherein said cervical cap is detachable from said cylindrical structure, the method further comprising the steps of:

d. detaching said cylindrical structure from said cervical cap; and e. removing said cylindrical structure from the patient.

38. The method according to claim 37, further comprising the step of:

f. removing said cervical cap from the patient.

39. The method according to claim 34, wherein said cervical agent delivery apparatus has an elongated tube passing through said cervical cap to said internal surface and a means for delivering the one or more cervical agents through said elongated tube, and zero or more therapeutic agents are contained on said internal surface of said cervical cap, the method further comprising the step of:

d. delivering one or more therapeutic agents with said means for delivering through said elongated tube onto said internal surface of said cervical cap.

40. The method according to claim 39, wherein said means for delivering is a syringe connected to said elongated tube, the method further comprising the step of:

e. filling said syringe with one or more therapeutic agents.

41. The method according to claim 39, wherein said means for delivering is a reservoir chamber adapted for containing the one or more therapeutic agents within said applicator and positioned between said elongated rod and said cylindrical device, said elongated tube connecting said reservoir chamber with said internal surface of said cervical cap.

42. The method according to claim 34, wherein one therapeutic agent is a cervical ripening compound, the method further comprising the step of:

d. leaving the cervical agent delivery apparatus in place within the patient with said cervical cap in contact with the patient's cervix for a desired amount of time.

43. The method according to claim 42, wherein the cervical ripening compound is about 25–100 micrograms of Misoprostol.

44. A method for dispensing one or more cervical agents to a patient's cervix, comprising the steps of:

a. inserting an applicator having an elongated rod and an elongated hollow tube with an internal chamber housing a cervical agent delivery apparatus into a patient's vaginal canal, said cervical agent delivery apparatus having a cylindrical structure with a front end and a back end, a cervical cap having an internal surface and being generally concave in shape, and an inflatable means for supporting said cervical cap, wherein said cervical cap is attached to said front end of said cylindrical structure and is adapted for having one or more cervical agents on said internal surface;

b. pushing said elongated rod of said applicator until said cervical agent delivery apparatus is deployed such that said cervical cap covers the patient's cervix;

c. removing said applicator from the patient; and d. inflating said inflatable means after said step (b).

45. The method according to claim 44, wherein said inflatable means is an inflatable ring attached to said front end of said cylindrical structure, an elongated tube having a first end connected to a bulb and a second end connected to said inflatable ring.

* * * * *